United States Patent [19]

Anapliotis

[11] Patent Number: 4,506,662

[45] Date of Patent: Mar. 26, 1985

[54] NAIL FOR FIXING A FRACTURE OF THE FEMUR

[75] Inventor: Emmanuel Anapliotis, Berlin, Fed. Rep. of Germany

[73] Assignee: Mecron medizinische Produkte GmbH, Berlin, Fed. Rep. of Germany

[21] Appl. No.: 390,079

[22] Filed: Jun. 18, 1982

[30] Foreign Application Priority Data

Jun. 18, 1981 [DE] Fed. Rep. of Germany ....... 3124059
Jul. 9, 1981 [DE] Fed. Rep. of Germany ....... 3127378

[51] Int. Cl.³ ............................ A61F 1/00; A61F 5/04
[52] U.S. Cl. ............................ 128/92 BC; 128/92 BA; 128/92 E; 3/19
[58] Field of Search ............ 128/92 B, 92 BB, 92 BC, 128/92 R, 92 CA, 92 E

[56] References Cited

U.S. PATENT DOCUMENTS 4,055,172 10/1977 Ender et al. ................... 128/92 BC

FOREIGN PATENT DOCUMENTS 7519604 11/1975 Fed. Rep. of Germany .
7519605 2/1976 Fed. Rep. of Germany .
2484242 12/1981 France ............................ 128/92 BB
576249 6/1976 Switzerland .................. 128/92 BC Primary Examiner—Richard J. Apley
Assistant Examiner—David Isabella
Attorney, Agent, or Firm—Spencer & Frank

[57] ABSTRACT

An elastic nail for fixing a bone fracture of the femur including an elongated cylindrical nail jacket having a distal end, a proximal end and an outer surface. The nail jacket is curved along its length between the distal and proximal ends and has a circular cross section between its ends with a region adjacent its distal end having a cross section which differs from the circular. The elasticity and curvature of the nail are such that when the nail is driven into the marrow cavity of the femur its distal end is supported by the cortical part of the bone. The region deviating from the circular cross section has a concave face and a convex face which are curved predominantly about axes extending parallel to the lengthwise direction of the nail jacket. The concave face forms a recess in the nail jacket, which recess is disposed at the inside of the curvature which relates to the entire length of the nail jacket. The convex face extends only slightly beyond the circular cross section transverse to the longitudinal direction of the nail jacket to form edge regions. Each edge region has a continuously curved surface joining the convex face to the concave face.

7 Claims, 8 Drawing Figures

NAIL FOR FIXING A FRACTURE OF THE FEMUR

BACKGROUND OF THE INVENTION

The invention relates to a bone nail, a tool for exerting a force or a torque, respectively, onto such a nail and an element for fixing the nail in the bone.

The principle of "bundle nailing" is described in the monograph entitled "Die Bündel-Nagelung" [Bundle Nailing] by K. H. Hackethal, Berlin, Göttingen, Heidelberg, 1961. This procedure results in a stable, true-to-form alignment of the marrow cavity by means of a plurality of elastic steel nails which are hammered in through an opening in the marrow cavity. The bundle of nails, which are usually bent, fills the marrow cavity completely or in part and, by spreading the nails in the region of the proximal end of the bundle, produces stabilization and thus maintains successful repositioning (idem, page 25, FIG. 13 and associated text). The bundle nailing process utilizes the spring effect of the nails which support themselves, inter alia, on the cortical part of the bone in the region of the window made for the introduction of the nails. Maintaining the initial tension in the nails after they are positioned is an important prerequisite for successful therapy.

All manipulations of the nails during insertion, positioning and extraction are made from their distal ends. Consequently, the following movements must be transmitted by way of the corresponding exertion of force:

1. insertion forces which act suddenly from the rear end of the nail in its longitudinal direction;
2. torques which are produced during insertion and enable the nail to be twisted while being driven in; and
3. retraction forces which enable the nail to be pulled out of the marrow cavity after the bone has healed.

The transmission of such forces requires special tools which must be of complicated design (idem, page 95, FIGS. 66 and 67) and which require space during use, a space which, due to the bundled arrangement of the nails, is available only to a limited degree.

German Auslegeschrift [Published Patent Application] No. 2,459,257 discloses a bone nail design which, according to the genus, has a distal end which is flattened in the form of a disc so that a plurality of nail ends can be arranged next to and above one another. The "disc-shaped flattening" offers the opportunity of transmitting torque during the insertion of the nail by means of a punch. This "disc-shaped flattening" is additionally intended to take care that the forces introduced into the bone as a result of the tension in the distal end of the nail are transmitted to the bone over an enlarged area.

Moreover, German Utility Model Pat. No. 7,519,604 discloses a bone nail having a region in the vicinity of its distal end where its cross section differs from the otherwise circular cross section of the nail for the purpose of introducing forces and/or moments during manipulation. The region of the nail deviating from the circular cross section has a concave face and a convex face which are curved predominantly about axes extending parallel to the longitudinal direction of the nail and in part extend beyond the nail's circular cross section. The nail is provided with a curvature and elasticity in such a manner that, when the nail is driven into the marrow cavity its distal end is supported by the cortical part of the bone.

This, last bone nail design however, does not consider that under surgical conditions it is not always possible to position the distal ends of the nails in such a manner that they rest smoothly against the cortical part of the bone; nor does it consider that the spring tension of the nail is introduced into the bone over the entire surface area of the flattened portion. Such optimum positioning is impossible in principle because the bundle nailing process is based on the principle that the tips of the nails spread out in space in the form of a fan along the trabeculae of the femur head so as to produce correct repositioning and stability of the fracture. Since the known nails having the disc-shaped flattened portions are provided with a curvature in the longitudinal direction of the nail, a curvature which is oriented in the same direction in all nails with respect to the flattened portions, there inevitably result positions for the disc-shaped flattened portions which deviate from a parallel shingle-like arrangement. This produces the danger that the narrow side of the flattened portion of the nails, which constitutes a sharp edge, exerts a chisel-like pressure onto the cortical part of the bone, thus raising the danger of perforation.

Since in their fixed state the distal ends of the nails project from the window opening made in the bone and utilize the edge of the window as a "back support", so that springing back into the marrow cavity is prevented, there exists the additional danger that, with less than optimum alignment of the flattened nail ends, these ends produce, in the region of their sharp edges, a skin ulceration with possible later infection.

SUMMARY OF THE INVENTION

It is an object of the invention to provide a design for the distal end of a bone nail which does not incorporate such a danger but which nevertheless permits the absorption of all forces to be transmitted during manipulation of the nail so that, particularly for osteoporotic bones, a breaking into the bone by the nail in the region of its cortical part is prevented.

These and other objects and advantages are accomplished in accordance with the invention wherein an elastic nail for fixing a bone fracture of the femur is provided including an elongated cylindrical nail jacket having a distal end, a proximal end and an outer surface. The nail jacket is curved along its length between the distal and proximal ends and has a circular cross section between its ends with a region adjacent its distal end having a cross section which differs from the circular. The elasticity and curvature of the nail are such that when the nail is driven into the marrow cavity of the femur its distal end is supported by the cortical part of the bone. The region deviating from the circular cross section has a concave face and a convex face which are curved predominantly about axes extending parallel to the lengthwise direction of the nail jacket. The concave face forms a recess in the nail jacket, which recess is disposed at the inside of the curvature which relates to the entire length of the nail jacket. The convex face extends only slightly beyond the circular cross section transverse to the logitudinal direction of the nail jacket to form edge regions. Each edge region has a continuously curved surface joining the convex face to the concave face.

The invention is based on the realization that a chisel-like effect on the surrounding bone or tissue regions can be prevented only if sharp-edged angular portions and high contact pressures are avoided. The solution achieved by the invention deviates from the principle that it is generally the custom in the art to select sharp-edged profiles (three, four or multi-edged designs) in order to transmit a torque by means of wrench-like tools. The invention, therefore, permits close bundle packing without creating chisel-like, narrow surface edges.

Since the recess is disposed at that side which is opposite the side intended, due to the curvature of the nail, to rest with its back against the cortical part of the bone when the nail has been inserted, interference with the bone is avoided with great certainty. By dimensioning the recess in such a manner that, in the circumferential direction, it encloses an arc corresponding to an angle of less than 120° on the cylinder jacket nail surface or is limited to a corresponding length in the longitudinal direction of the nail, the nail, when in the inserted state, is able to take on almost any position without producing an unduly high areal pressure which would endanger the cortical part of the bone.

A particular advantage of the solution according to the invention is, in addition to the fact that only uncomplicated tools are required to produce bone nails of such design, that their manipulation is likewise possible by means of devices of simple design. For example, a cylindrically rounded recess can be produced without complications by cold working and, in one process step, an elliptical or oval configuration of the nail cross section can be produced in the region of the recess so that a torque can be transmitted by attaching a simple tool.

Preferably, the recess is further provided with a passage opening which leads to a region on the surface of the nail disposed opposite the locus of the recess, with the passage opening having a cross section which is considerably smaller than the nail surface region occupied by the recess so that a pin can be accommodated to guide or center the tool during manipulation of the nail.

A tool for retracting, or exerting a torque onto, a nail according to the invention is preferably provided with a jaw which has a raised portion adapted to the recess so that transmission of torque and force can take place without the nail having to be provided with projections with sharp edges that would endanger the cortical part of the bone. This jaw includes a surface with which a retracting force can be exerted onto that face of the recess which forms part of the cross-sectional area of the nail.

Favorably, the tool is provided with a blocking element which is supported on the part of the cylinder jacket shaped surface of the distal nail end opposite the recess and keeps the above-mentioned faces in mutual engagement. The blocking element is here formed by a tongue or, if the tool is given a forceps shape, by a counterjaw and/or by a displaceable bolt.

The invention solves the problem, in particular, that for bundle nailing the bone nails must be arranged in the most space saving manner, with the shaping elements required to exert the forces on the nail during insertion or retraction of the nail given such a design that they take up only insignificantly more space.

Moreover, another advantage in the nail according to the invention is that the position of the nails in the bone can be fixed by means of simple elements which engage into the recess and are adapted to its shape. When the nails are inserted, this recess is accessible from the exterior of the bone so that manipulation is facilitated in this respect.

In the bundle nailing process, it is preferred to effect a "seal" by means of bone cement, with the not yet hardened cement mass being able to connect a plurality of recesses of nails with the adjacent bone substance. Since the bone cement enters into the recesses with a cross section which is able to absorb the corresponding shearing stresses, movement of the nails in the longitudinal direction is prevented with certainty.

In cases where individual nails are employed with preference, a fixing element is favorable which is designed as a plate provided with holes for bone screws and with at least one raised portion which is adapted for engagement in the recess.

Advantageous modifications of the invention are defined in the dependent claims or will be described in greater detail, respectively, in the description below of a preferred embodiment of the invention.

BRIEF DESCRIPTION OF THE DRAWINGS

FIG. 2b shows a bundle arrangement of a plurality of the nails shown in FIG. 2a.

DESCRIPTION OF THE PREFERRED EMBODIMENTS

Figure 1:
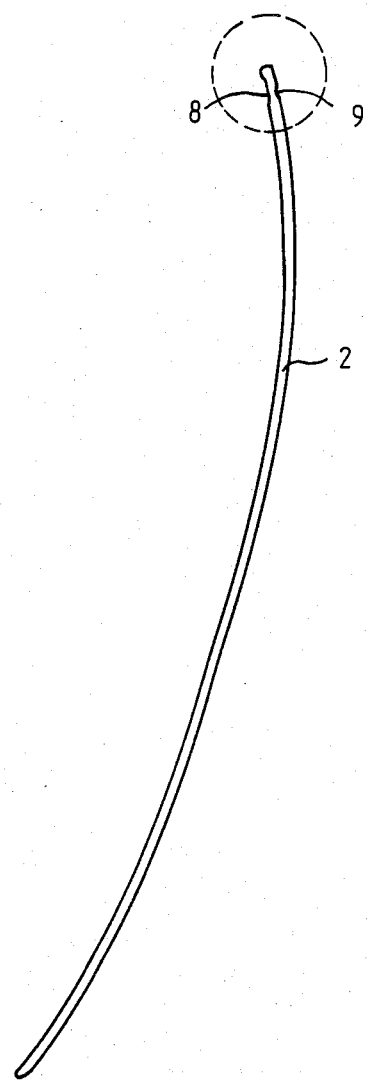
FIG. 1 is a side view of an embodiment of the bone nail according to the invention.
Figures 1A, 1B, 1C:
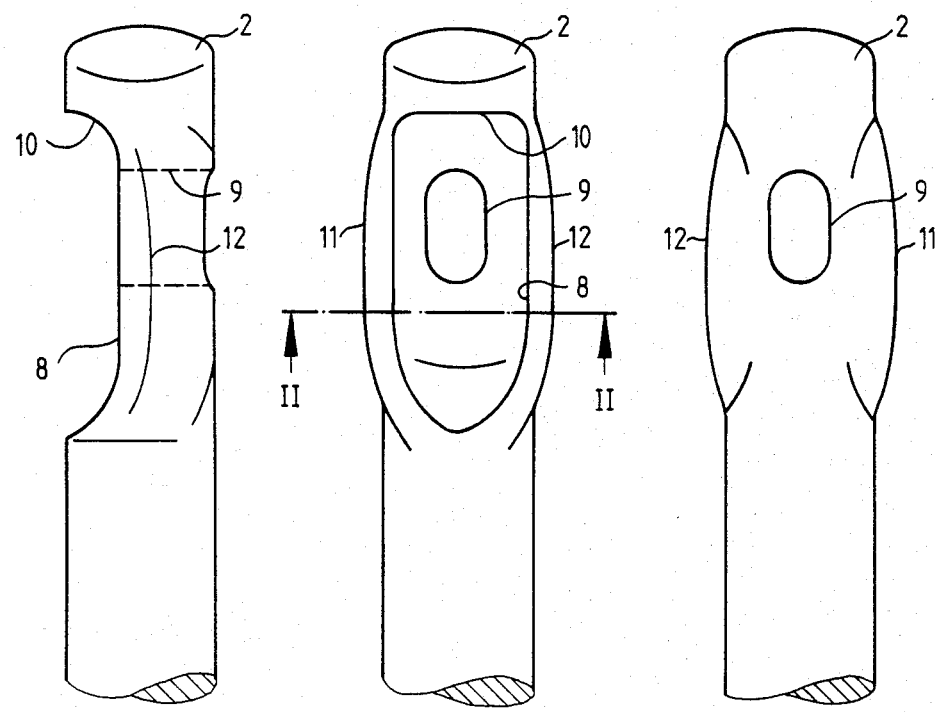
FIGS. 1a through c illustrate three enlarged side views of the distal end of one embodiment of the nail according to the invention.

FIG. 1 shows a curved nail 2 with the region covered by and shown to an enlarged scale in FIGS. 1a through 1c being enclosed by a dashed line. A recess 8 in the nail 2 is disposed at the interior of the nail curvature. This curvature may be composed of various bends and angles which are distributed over the entire length of the nail, so that, if the nail is used to fix fractures of the neck of the femur, the end of the nail provided with the recess 8 rests gently with its rear side, that is the side opposite the recess, against the cortical part of the bone.

The distal end of the nail 2 according to the invention, which is shown to an enlarged scale in FIGS. 1a through 1c, has a semicircular recess 8 whose rounded portion extends in the direction of the roundness of the nail surface. This recess is offset with respect to the extreme outer end of the nail. In its edge regions extending in the longitudinal direction of the nail, the recess 8 changes in a softly curved way into the cylinder jacket face of the nail. At the bottom of the recess, there is provided a passage opening 9, which forms a passage to the oppositely disposed region of the nail jacket surface and occupies a smaller area than the recess. The recess 8 has an upper limiting face 10 which extends essentially horizontally. The region of the passage opening 9 near the distal end of the nail is shaped to upper limiting face 10 or follows it directly or via a step. Regions 11 and 12 serve to introduce a torque and are provided to the sides of recess 8.

Figure 2A:
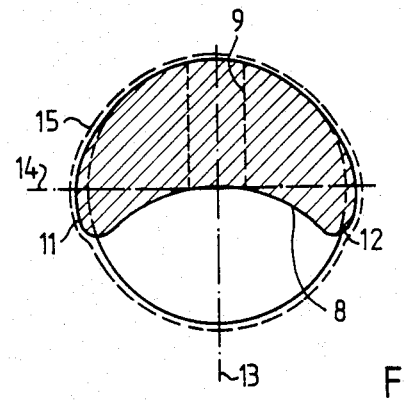
FIG. 2a is a cross-sectional view of taken along line II—II in FIG. 1b.

FIG. 2a shows the bone nail of FIGS. 1 through 1c in a cross-sectional view. The plane of the section is marked II in FIG. 1b. The recess 8 has here been produced by cold working in such a manner that the regions 11 and 12 extend beyond the circular nail cross section and are arranged in symmetry with respect to the line 13 which is shown by dots and dashes and represents a diameter. The regions 11 and 12 which are convex and do not change their cross section over a path in the longitudinal direction of the nail or do not exceed a maximum outer contour, respectively, are additionally formed, in the region extending beyond the circular cross section of the nail, symmetrically into a line 14 which, is also shown in dots and dashes, so that access for a tool is made possible. The interior outline of such a tool is indicated by a dashed line 15. The tool can easily be attached and manipulated in this manner, which can, moreover, be realized also by arranging the regions 11 and 12 in rotational symmetry (by 180°).

This sectional view shows that the cross section of the nail deviates slightly from the shape of a circular disc in the region of its recess 8, not including the recess 8 itself and the passage opening 9. The cross sectional shape is preferbly slightly elliptical or oval or triangularly rounded and, in the case of an elliptical configuration, the axial ratio is preferably selected to lie in a range between 1:1.1 and 1:1.2, and the longer half axis is oriented parallel to that surface region at which the recess 8 is provided. Such a slightly eccentric deformation of the nail end cross section in the region of the recess 8 can be realized, according to a preferred manufacturing process for the nail according to the invention, in that the recess is struck by way of cold working. The resulting eccentricity is sufficient to exert a torque during driving in of the nail by means of a suitably adapted sleeve to be placed over the nail so as to enable the nail to be positively guided with respect to the direction to be taken by its proximal end.

FIG. 2a also shows that the recess 8 is arranged in such a manner that, due to the rounded shape provided by the invention, it has no edges or faces in its lateral regions which could exert a chisel-like pressure on bone or tissue portions. Such an effect produced by closely adjacent surface portions with the resulting high contact pressures on bone or tissue regions is also prevented in that the recess 8 is not disposed directly at the end of the nail. Rather, it is offset backwardly by a slight distance from the end of the nail so that, at the immediate end of the nail, there exists an essentially undeformed region of the nail surface which can be supported over a large area by the bone or the tissue, respectively.

The outer face of the nail disposed opposite the recess 8 forms a region which assures secure contact at the upper edge of the bone window (not shown) even if the nail is inserted with an axial twist of more than ±90°. Due to the relatively slight deviation of the nail end from the circular cross section, it is possible to arranged the nails in parallel in a bundled position even in the region of the recess 8 without requiring noticeably more space.

Figure 2B:
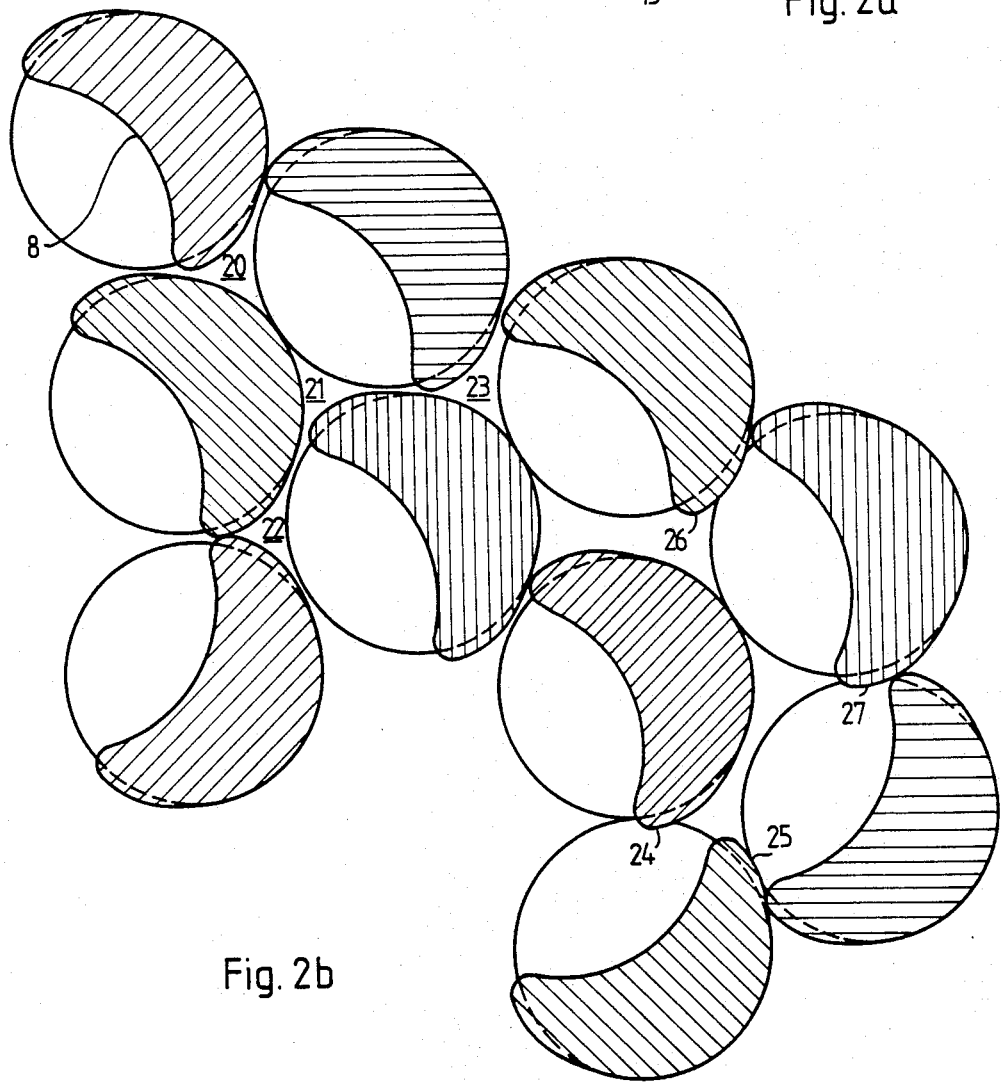

FIG. 2b is a sectional view of a plurality of nails 8 in an arbitrary bundle-like arrangement, it being intended to show at the various regions of contact between adjacent nails that, in spite of the regions 11 and 12 which project beyond the circular cross section of the nails, it is possible to arrange the nails in such a manner that the treating surgeon need not take particular care to accurately align the nails with respect to the direction of the recesses 8. Rather, it is possible to produce a tight bundle pack even if the individual nails are arranged to differ by angular amounts.

The regions 11 and 12 of the nails 2 which exceed the circular cross section here extend in the loci of cavities 21 to 25 existing between adjacent, closely juxtaposed nails. The regions 11 and 12 extend into the areas not otherwise filled by material between the circular cross setions of the nails so that the nails may be arranged in the tightest possible pack. Region 22 accommodates the curved regions of two nails in the recess portion left by the juxtaposition of three nails and these curved regions also do not interfere with one another.

FIG. 2b shows that contact of the distal nail ends with the cortical part of the bone need not take place along a straight line but that here again it is possible without difficulty to follow a curvature. (The demarkation line for the space available for the nailing process can here be imagined to be the line touching the nail shown at the top of FIG. 2b.) The illustrated advantages of the space saving arrangement with tight bundle packing also applies to the corresponding regions in the region of the opposite nail ends (not shown in the drawings).

It must further be pointed out that the space available between the circular cross sections of the nails can be occupied by the convex regions 11 and 12 even if the recesses 8 are not at the same height.

Figure 3:
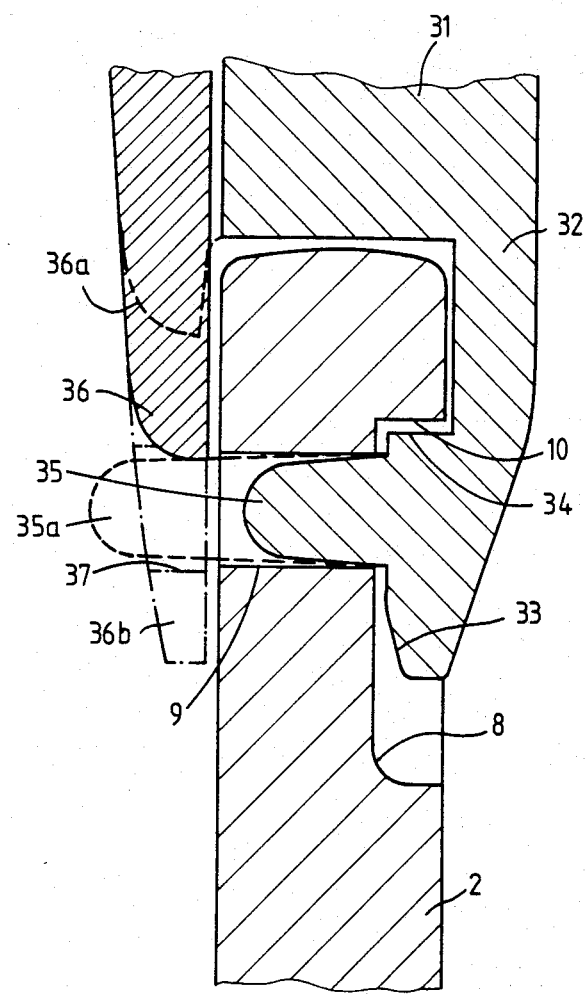
FIG. 3 is a sectional view of a tool for exerting a force or a torque, respectively, onto a nail according to the invention.

FIG. 3 shows the lower region of a tool 31 which is in engagement with the distal end of the nail 2 in order to exert compressive and tension forces or torques. The drawing figure shows several variations in dashed lines, such as can be used in different combinations.

If the end of a nail 2 is oval or elliptical in the region of the recess, it is advisable to use an instrument such as a striking iron, which (in deviation from the shape shown in FIG. 3) includes a recess that is adapted to the noncircular shape of the nail end and thus is able to transmit the moments required to rotate the nail during drivig in.

On the other hand, tool configurations as shown in FIG. 3 can be used for noncircular as well as circular cross sections for rotating insertion as well as for retraction of the nail.

One supporting member 32 for the tool 31 is provided with a hook-shaped extension which is equipped with a jaw 33 adapted to the recess 8. A face 34 which acts on face 10 of nail 2 permits retraction of the nail from the bone when the healing process is completed.

To guide the hook-shaped end of member 32 of the tool 31 when the distal end of the nail 2 is gripped, a pin 35 is provided which may have various lengths (dashed line 35a) and which has a rounded free end so as to facilitate insertion into recess 9.

In order to prevent the hook-shaped extension and its face 34 on tool 31 from slipping off when a torque is exerted or during retraction, a block 36 is provided at the part of the tool 31 coming in contact with the recess 8. This block may have various shapes. The variation shown as a solid line may be designed in the form of a bolt which can be operated from the upper end of the tool (not shown) and displaced in the direction of the nail 2 or it may represent the counterjaw of a forceps with which the distal end of the nail 2 can be gripped.

On the other hand, the variation shown in dashed lines 36a is fixed to the opposite side of the tool 31 engaging in recess 8, but is shorter and is designed to be slightly rounded so that the tool 31, which is designed in one stationary piece, can be "capped" over the end of the nail with a tilt to the side. If the tool 31 is guided coaxially with the nail, part 33 which engages in recess 8 is safely prevented from slipping off.

If the tool 31 is designed in the form of a forceps, a variation is favorable which is shown as the dot-dash line 36b. The extended design of this variation is provided with an opening 37 which comes into engagement with the extended pin 35a so that in cases where the forces required to extract the nail are particularly high, the tightness of the connection of tool/nail is additionally augmented.

Figure 4:
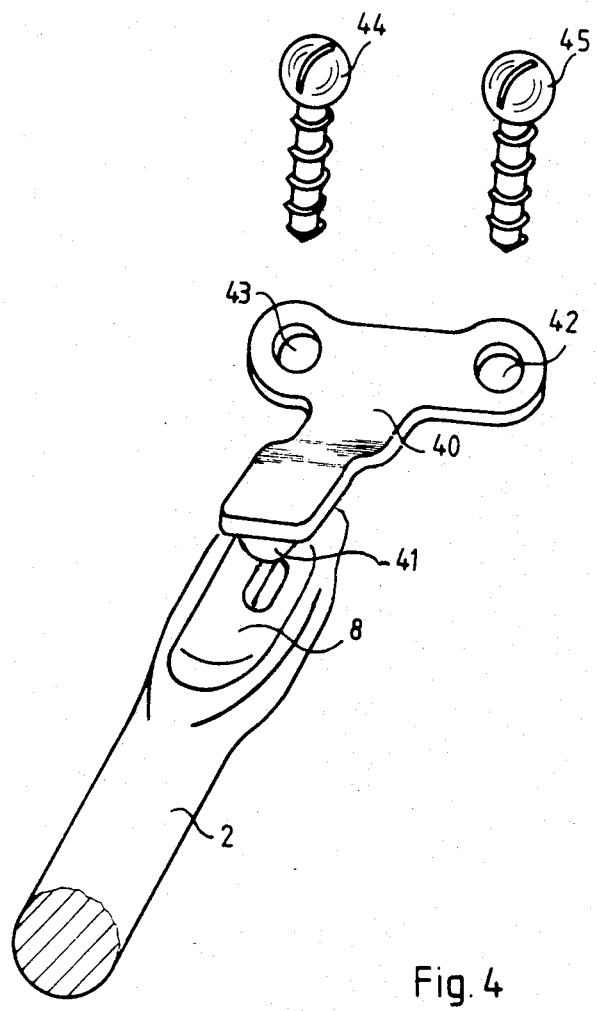
FIG. 4 shows a fixing element for a nail according to the invention.

FIG. 4 shows a fixing element 40 in conjunction with a nail 2 with the fixing element representing a plate provided with a tongue-shaped extension 41 which is shaped to engage in the recess 8 of the nail. The rounding of tongue 41 assures simple insertion and the secure engagement in the fixed state is assured by the contact pressure force exerted by the plate. For this purpose, the plate is provided with two round recesses 42 and 43, into which bone screws 44 and 45 can be inserted so as to hold the fixing element 40. To remove the nail, the fixing element 40 can be released in a simple manner.

In addition to the illustrated exemplary embodiments, the invention permits a plurality of further variations, where the tool for manipulating the nail and the fixing element can be designed correspondingly multifacetedly.

I claim:

1. An elastic nail for fixing a bone fracture of the femur, said nail comprising an elongated cylindrical rod having a distal end, a proximal end and an outer surface, said rod being curved along its length between said distal and proximal ends, the elasticity and curvature of said rod being such that when said rod is driven into the marrow cavity of the femur its distal end is supported by the cortical part of the bone, said rod having a circular cross section between its ends, with a region integral with said rod and adjacent its distal end having a cross section which differs from circular, said region having a concave face and a convex face which are curved predominantly about axes extending parallel to the lengthwise direction of said rod, said concave face defining a recess in the outer surface of said rod, said recess being disposed at the inside of the curvature which relates to the entire length of said rod, said convex face extending only in part slightly beyond said circular cross section transverse to the longitudinal direction of said rod to form edge regions each of which has a continuously curved surface joining said convex face to said concave face thereby preventing chisel-like pressure onto the cortical part of the bone.

2. A nail according to claim 1 wherein said edge regions each extend beyond the circular cross section of said rod to form respective projections which serve as working surfaces for the transmission of torques on said nail.

3. A nail according to claim 2 wherein each said projection has a mid-point in the circumferential direction and said mid-points are angularly spaced from each other by substantially 180 degrees with respect to the lengthwise direction of said rod.

4. A nail according to claim 1 wherein said recess is provided with a planar face substantially at a right angle with the lengthwise direction of said rod and which constitutes a delimitation of said recess toward said distal end.

5. A nail according to claim 1 wherein said recess is provided with a passage opening which leads to the outer surface of said rod opposite said concave face, said passage opening having a cross section which is substantially smaller than the portion of said region occupied by said recess.

6. A nail according to claim 2, wherein, in the circumferential direction of said region, said concave face encloses an arc of 120° and said convex face covers an arc of 240°.

7. A fixing element in combination with a bone nail, the bone nail including an elongated cylindrical rod having a distal end, a proximal end and an outer surface, the rod being curved along its length between the distal and proximal ends and having a circular cross section between its ends with a region integral with the rod and adjacent its distal end having a cross section which differs from circular, the region having a concave face and a convex face which are curved predominantly about axes extending parallel to the lenghtwise direction of the rod, the concave face defining a recess in the outer surface of the rod at the inside of the curvature which relates to the entire length of the rod, the convex face extending only in part slightly beyond the circular cross section to form a recess having edge regions, each edge region having a continuously curved surface joining the convex face to the concave face, said fixing element comprising:
a plate provided with a tongue-shaped extension which is shaped to engage the recess in the outer surface of the rod and holes for receiving bone screws.

* * * * *